United States Patent
Detjen et al.

(10) Patent No.: US 10,961,168 B2
(45) Date of Patent: Mar. 30, 2021

(54) USE OF LIGHT GAS BY-PRODUCTS IN THE PRODUCTION OF PARAXYLENE BY THE METHYLATION OF TOLUENE AND OR BENZENE

(71) Applicant: ExxonMobil Chemical Patents Inc., Baytown, TX (US)

(72) Inventors: Todd E. Detjen, Houston, TX (US); Robert G. Tinger, Friendswood, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 16/335,581

(22) PCT Filed: Aug. 2, 2017

(86) PCT No.: PCT/US2017/045097
§ 371 (c)(1),
(2) Date: Mar. 21, 2019

(87) PCT Pub. No.: WO2018/057125
PCT Pub. Date: Mar. 29, 2018

(65) Prior Publication Data
US 2020/0017425 A1    Jan. 16, 2020

Related U.S. Application Data

(60) Provisional application No. 62/398,252, filed on Sep. 22, 2016.

(30) Foreign Application Priority Data

Nov. 4, 2016    (EP) ..................................... 16197276

(51) Int. Cl.
C07C 2/86    (2006.01)
C07C 2/54    (2006.01)
B01J 8/00    (2006.01)
B01J 8/18    (2006.01)

(52) U.S. Cl.
CPC ............ C07C 2/865 (2013.01); B01J 8/0055 (2013.01); B01J 8/1827 (2013.01); C07C 2/864 (2013.01); B01J 2208/00761 (2013.01); B01J 2208/00893 (2013.01); C07C 2529/40 (2013.01); C07C 2529/65 (2013.01)

(58) Field of Classification Search
CPC .... C07C 2/86; C07C 2/56; C07C 2/64; C07C 2/66
See application file for complete search history.

(56) References Cited

U.S. PATENT DOCUMENTS

| | | |
|---|---|---|
| 4,002,698 A | 1/1977 | Kaeding |
| 4,356,338 A | 10/1982 | Young |
| 4,423,266 A | 12/1983 | Young |
| 5,675,047 A | 10/1997 | Beck et al. |
| 5,804,690 A | 9/1998 | Chang et al. |
| 5,939,597 A * | 8/1999 | Dessau .................. C07C 2/861 585/447 |
| 6,028,238 A | 2/2000 | Beck et al. |
| 6,046,372 A | 4/2000 | Brown et al. |
| 6,048,816 A | 4/2000 | Brown et al. |
| 6,156,949 A | 12/2000 | Brown et al. |
| 6,423,879 B1 * | 7/2002 | Brown ..................... B01J 29/40 502/245 |
| 6,504,072 B1 * | 1/2003 | Brown ..................... B01J 29/40 585/464 |
| 6,506,954 B1 | 1/2003 | Brown et al. |
| 6,538,167 B1 | 3/2003 | Brown et al. |
| 6,642,426 B1 * | 11/2003 | Johnson .................. C07C 2/864 585/446 |
| 2015/0073187 A1 * | 3/2015 | Ghosh ....................... C07C 2/66 585/321 |

FOREIGN PATENT DOCUMENTS

| | | | |
|---|---|---|---|
| WO | 2013/052260 | 4/2013 | |
| WO | WO2013052260 A1 * | 4/2013 | ............... C07C 2/64 |
| WO | 2016/032636 | 3/2016 | |

* cited by examiner

Primary Examiner — Youngsul Jeong

(57) ABSTRACT

A process for producing paraxylene by the catalytic alkylation of benzene and/or toluene with methanol, which produces a para-rich mixture of xylene isomers, together with water and some light organic by-products, particularly dimethyl ether and $C_{4-}$ olefins. The off-gas stream, containing the $C_{4-}$ olefins, may be recycled back to the reaction to be co-injected with methanol to reduce the methanol self-decomposition and the reaction of methanol to olefins or to fluidize catalyst particles recovered by a reactor cyclone. By using recycled off-gas rather than water or steam, the deleterious effects of water and/or steam on the catalyst aging and activity rates and the size of downstream equipment necessary to recover olefin by-products may be reduced.

15 Claims, 1 Drawing Sheet

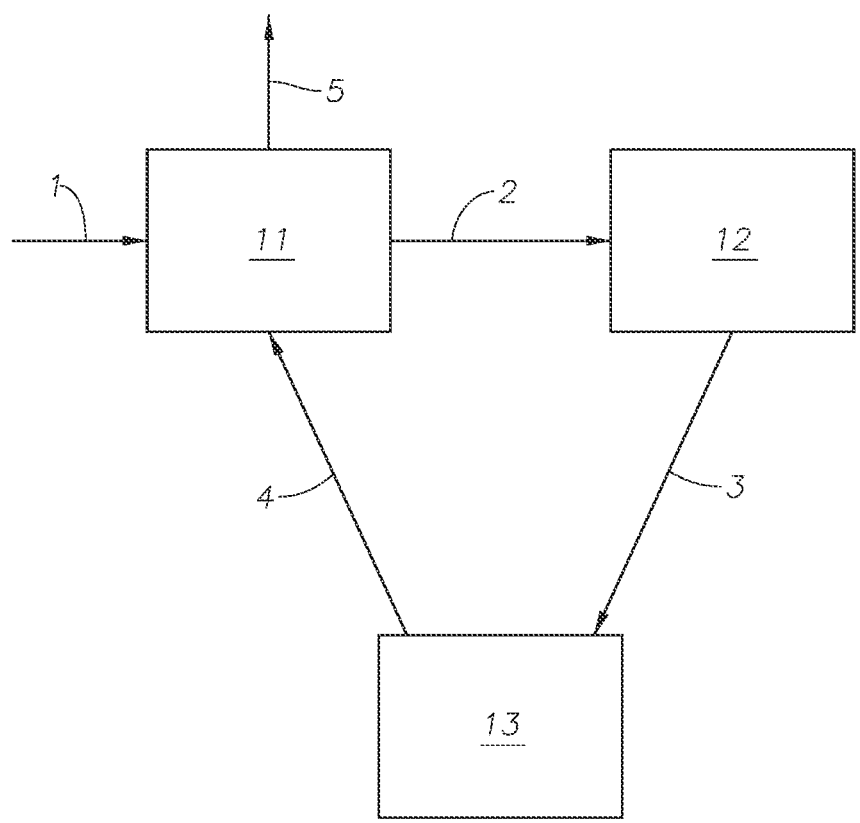
(Prior Art)

USE OF LIGHT GAS BY-PRODUCTS IN THE PRODUCTION OF PARAXYLENE BY THE METHYLATION OF TOLUENE AND OR BENZENE

PRIORITY CLAIM

This application is National Phase application of PCT/US2017/045097, filed Aug. 2, 2017 and claims the benefit of and priority to Provisional Application No. 62/398,252, filed Sep. 22, 2016 and European Application No. 16197276.5, filed Nov. 04, 2016, the disclosures of which are incorporated herein by reference in their entirety.

TECHNICAL FIELD

This disclosure relates to a process for utilizing off-gas produced in the production of paraxylene by the alkylation of benzene and/or toluene with methanol.

BACKGROUND

Of the xylene isomers, paraxylene is of particular value since it is useful in the manufacture of terephthalic acid, which is an intermediate in the manufacture of synthetic fibers and resins. Today, paraxylene is commercially produced by hydrotreating of naphtha (catalytic reforming), steam cracking of naphtha or gas oil, and toluene disproportionation.

One problem with most existing processes for producing xylenes is that they produce a thermodynamic equilibrium mixture of ortho-xylene, meta-xylene and para-xylene (referred to herein as OX, MX, and PX, respectively), in which the PX concentration is typically only about 24 wt %. Thus, separation of PX from such mixtures tends to require superfractionation and multistage refrigeration steps. Such processes involve high operating and capital costs and result in only limited yields. Therefore, there is a continuing need to provide processes which are highly selective for the production of PX.

It is well-known to manufacture xylenes by the alkylation of toluene and/or benzene with methanol, and, in particular, to selectively make PX product using zeolite catalyst. See, for instance, U.S. Pat. Nos. 4,002,698; 4,356,338; 4,423,266; 5,675,047; 5,804,690; 5,939,597; 6,028,238; 6,046,372; 6,048,816; 6,156,949; 6,423,879; 6,504,072; 6,506,954; 6,538,167; and 6,642,426. The terms "paraxylene selectivity", "para-selective", and the like, means that PX is produced in amounts greater than is present in a mixture of xylene isomers at thermodynamic equilibrium, which at ordinary processing temperatures is about 24 mol %. PX selectivity is highly sought after because of the economic importance of PX relative to MX and OX. Although each of the xylene isomers have important and well-known end uses, PX is currently the most economically valuable.

In the process, typically toluene and/or benzene are alkylated with methanol, in the presence of a suitable catalyst, to form xylenes in a reactor in a system illustrated schematically in the FIGURE, wherein a feed comprising reactants enter fluid bed reactor 11 via conduit 1 and effluent comprising product exits through conduit 5, and the catalyst circulates between fluid bed reactor 11, apparatus 12, which strips fluid from the catalyst, and catalyst regenerator 13, via conduits 2, 3, and 4, respectively. Water is typically co-fed with toluene and methanol to minimize toluene coking in the feed lines and methanol self-decomposition. Other side reactions include the formation of light olefins, light paraffins, as reactions that convert PX to other xylene isomers or heavier aromatics.

While co-feeding water into the reaction is beneficial in reducing the methanol self-decomposition and the reaction of methanol to olefins, the steam created by the water can negatively impact the aging and activity rate of the catalyst. Additionally, the process inevitably produces significant quantities of light ($C_{4-}$) gas. These gaseous by-products include olefins, particularly ethylene, propylene and butylenes; alkanes, such as methane, ethane, propane and butanes, which may be recovered and purified to increase their value above fuel value.

Thus, it is desirable to increase the efficiency of the methylation of benzene and/or toluene process and extend the catalyst life.

BRIEF SUMMARY

Embodiments disclosed herein provide a process for producing PX by the catalytic alkylation of benzene and/or toluene with methanol. The alkylation process produces a PX-rich mixture of xylene isomers, together with water and some light organic by-products, particularly dimethyl ether and $C_{4-}$ olefins. The off-gas stream, containing the $C_{4-}$ olefins, may be recycled back to the reaction to be co-injected with methanol to reduce the methanol self-decomposition and the reaction of methanol to olefins or to fluidize catalyst particles recovered by the reactor cyclone. By using recycled off-gas rather than water or steam, the deleterious effects of water and/or steam on the catalyst aging and activity rates and the size of downstream equipment necessary to recover olefin by-products may be reduced.

In one embodiment, the process for the alkylation of toluene and/or benzene to produce PX comprises contact of toluene and/or benzene with an alkylating agent selected from methanol, dimethyl ether, and mixtures thereof, in the presence of an alkylation catalyst in a fluidized bed alkylation reactor under conditions effective to produce an alkylation effluent comprising PX and light gas by-products including olefins. The alkylation effluent is separated into a stream comprising PX and a light gas stream, and at least a portion of the light gas stream including olefins is recycled to the alkylation reactor for injection with alkylating agent, fluidizing particles of the alkylation catalyst recovered from the alkylation effluent, or both.

Other embodiments are directed to a process for producing PX in which toluene and/or benzene are contacted with methanol in the presence of an alkylation catalyst in an alkylation reactor under conditions effective to produce an alkylation effluent comprising PX and a light gas by-products including olefins. The alkylation effluent is separated into a product stream containing PX and a light gas stream containing the light gas by-products. PX is recovered from the product stream, and at least a portion of the light gas stream including olefins are recycled to the alkylation reactor for at least one of: injection with the methanol, fluidizing particles of the alkylation catalyst recovered from the alkylation effluent, or both.

BRIEF DESCRIPTION OF THE DRAWING

The FIGURE is a schematic of a reactor system including reactor and regenerator and some associated auxiliary devices and transfer piping per se known in the art.

DETAILED DESCRIPTION OF THE EMBODIMENTS

Described herein is a process for producing PX by the catalytic alkylation of benzene and/or toluene with methanol. The alkylation process produces a PX-rich mixture of xylene isomers, together with water and some light organic by-products, particularly dimethyl ether and $C_{4-}$ olefins. The off-gas stream, containing the $C_{4-}$ olefins, may be recycled back to the reaction to be co-injected with methanol to reduce the methanol self-decomposition and the reaction of methanol to olefins or to fluidize catalyst particles recovered by the internal reactor cyclone. By using recycled off-gas rather than water or steam, the deleterious effects of water and/or steam on the catalyst aging and activity rates and the size of downstream equipment necessary to recover olefin by-products may be reduced.

The alkylation process employed herein can employ any aromatic feedstock comprising benzene and/or toluene, although in general it is preferred that the aromatic feed contains at least 90 wt %, especially at least 99 wt %, of toluene. Similarly, although the composition of the methanol-containing feed is not critical, it is generally desirable to employ feeds containing at least 90 wt %, especially at least 99 wt %, of methanol.

The catalyst employed in the alkylation process is generally a porous crystalline material and, in one preferred embodiment, is a porous crystalline material having a Diffusion Parameter for 2,2 dimethylbutane of about 0.1-15 $sec^{-1}$ when measured at a temperature of 120° C. and a 2,2 dimethylbutane pressure of 60 torr (8 kPa).

As used herein, the Diffusion Parameter of a particular porous crystalline material is defined as $D/r^2 \times 10^6$, wherein D is the diffusion coefficient ($cm^2/sec$) and r is the crystal radius (cm). The diffusion parameter can be derived from sorption measurements provided the assumption is made that the plane sheet model describes the diffusion process. Thus, for a given sorbate loading Q, the value $Q/Q_{eq}$, where $Q_{eq}$ is the equilibrium sorbate loading, is mathematically related to $(Dt/r^2)^{1/2}$ where t is the time (sec) required to reach the sorbate loading Q. Graphical solutions for the plane sheet model are given by J. Crank in "The Mathematics of Diffusion", Oxford University Press, Ely House, London, 1967.

The porous crystalline material is preferably a medium-pore size aluminosilicate zeolite. Medium pore zeolites are generally defined as those having a pore size of about 5 to about 7 Angstroms, such that the zeolite freely sorbs molecules such as n-hexane, 3-methylpentane, benzene, and PX. Another common definition for medium pore zeolites involves the Constraint Index test which is described in U.S. Pat. No. 4,016,218, which is incorporated herein by reference. In this case, medium pore zeolites have a Constraint Index of about 1-12, as measured on the zeolite alone without the introduction of oxide modifiers and prior to any steaming to adjust the diffusivity of the catalyst. In addition to the medium-pore size aluminosilicate zeolites, other medium pore acidic metallosilicates, such as silicoaluminophosphates (SAPOs), can be used in the present process.

Particular examples of suitable medium pore zeolites include ZSM-5, ZSM-11, ZSM-12, ZSM-22, ZSM-23, ZSM-35, and ZSM-48, with ZSM-5 and ZSM-11 being particularly preferred. In one embodiment, the zeolite employed in the processes disclosed herein is ZSM-5 having a silica to alumina molar ratio of at least 250, as measured prior to any treatment of the zeolite to adjust its diffusivity.

Zeolite ZSM-5 and the conventional preparation thereof are described in U.S. Pat. No. 3,702,886. Zeolite ZSM-11 and the conventional preparation thereof are described in U.S. Pat. No. 3,709,979. Zeolite ZSM-12 and the conventional preparation thereof are described in U.S. Pat. No. 3,832,449. Zeolite ZSM-23 and the conventional preparation thereof are described in U.S. Pat. No. 4,076,842. Zeolite ZSM-35 and the conventional preparation thereof are described in U.S. Pat. No. 4,016,245. ZSM-48 and the conventional preparation thereof are taught by U.S. Pat. No. 4,375,573. The entire disclosures of these U.S. patents are incorporated herein by reference.

The medium pore zeolites described above are preferred for the present process since the size and shape of their pores favor the production of PX over the other xylene isomers. However, conventional forms of these zeolites have Diffusion Parameter values in excess of the 0.1-15 $sec^{-1}$ range desired for the present process. Nevertheless, the required diffusivity can be achieved by severely steaming the zeolite so as to effect a controlled reduction in the micropore volume of the catalyst to not less than 50%, and preferably 50-90%, of that of the unsteamed catalyst. Reduction in micropore volume is monitored by measuring the n-hexane adsorption capacity of the zeolite, before and after steaming, at 90° C. and 75 torr n-hexane pressure.

Steaming to achieve the desired reduction in the micropore volume of the porous crystalline material can be effected by heating the material in the presence of steam at a temperature of at least about 950° C., preferably about 950 to about 1075° C., and most preferably about 1000 to about 1050° C. for about 10 minutes to about 10 hours, preferably from 30 minutes to 5 hours.

To effect the desired controlled reduction in diffusivity and micropore volume, it may be desirable to combine the porous crystalline material, prior to steaming, with at least one oxide modifier, preferably selected from oxides of the elements of Groups IIA, IIIA, IIIB, IVA, VA, VB and VIA of the Periodic Table (IUPAC version). Conveniently, said at least one oxide modifier is selected from oxides of boron, magnesium, calcium, lanthanum and preferably phosphorus. In some cases, it may be desirable to combine the porous crystalline material with more than one oxide modifier, for example a combination of phosphorus with calcium and/or magnesium, since in this way it may be possible to reduce the steaming severity needed to achieve a target diffusivity value. The total amount of oxide modifier present in the catalyst, as measured on an elemental basis, may be between about 0.05 and about 20 wt %, such as between about 0.1 and about 10 wt %, based on the weight of the final catalyst.

Where the modifier includes phosphorus, incorporation of modifier in the alkylation catalyst is conveniently achieved by the methods described in U.S. Pat. Nos. 4,356,338; 5,110,776; 5,231,064 and 5,348,643, the entire disclosures of which are incorporated herein by reference. Treatment with phosphorus-containing compounds can readily be accomplished by contacting the porous crystalline material, either alone or in combination with a binder or matrix material, with a solution of an appropriate phosphorus compound, followed by drying and calcining to convert the phosphorus to its oxide form. Contact with the phosphorus-containing compound is generally conducted at a temperature of about 25° C. and about 125° C. for a time between about 15 minutes and about 20 hours. The concentration of the phosphorus in the contact mixture may be between about 0.01 and about 30 wt %.

Representative phosphorus-containing compounds which may be used to incorporate a phosphorus oxide modifier into the catalysts disclosed herein include derivatives of groups represented by $PX_3$, $RPX_2$, $R_2PX$, $R_3P$, $X_3PO$, $(XO)_3PO$, $(XO)_3P$, $R_3P=O$, $R_3P=S$, $RPO_2$, $RPS_2$, $RP(O)(OX)_2$, $RP(S)(SX)_2$, $R_2P(O)OX$, $R_2P(S)SX$, $RP(OX)_2$, $RP(SX)_2$, $ROP(OX)_2$, $RSP(SX)_2$, $(RS)_2PSP(SR)_2$, and $(RO)_2POP(OR)_2$, where R is an alkyl or aryl, such as phenyl radical, and X is hydrogen, R, or halide. These compounds include primary, $RPH_2$, secondary, $R_2PH$, and tertiary, $R_3P$, phosphines such as butyl phosphine, the tertiary phosphine oxides, $R_3PO$, such as tributyl phosphine oxide, the tertiary phosphine sulfides, $R_3PS$, the primary, $RP(O)(OX)_2$, and secondary, $R_2P(O)OX$, phosphonic acids such as benzene phosphonic acid, the corresponding sulfur derivatives such as $RP(S)(SX)_2$ and $R_2P(S)SX$, the esters of the phosphonic acids such as dialkyl phosphonate, $(RO)_2P(O)H$, dialkyl alkyl phosphonates, $(RO)_2P(O)R$, and alkyl dialkylphosphinates, $(RO)P(O)R_2$; phosphinous acids, $R_2POX$, such as diethylphosphinous acid, primary, $(RO)P(OX)_2$, secondary, $(RO)_2POX$, and tertiary, $(RO)_3P$, phosphites, and esters thereof such as the monopropyl ester, alkyl dialkylphosphinites, $(RO)PR_2$, and dialkyl alkyphosphinite, $(RO)_2PR$, esters. Corresponding sulfur derivatives may also be employed including $(RS)_2P(S)H$, $(RS)_2P(S)R$, $(RS)P(S)R_2$, $R_2PSX$, $(RS)P(SX)_2$, $(RS)_2PSX$, $(RS)_3P$, $(RS)PR_2$, and $(RS)_2PR$. Examples of phosphite esters include trimethylphosphite, triethylphosphite, diisopropylphosphite, butylphosphite, and pyrophosphites such as tetraethylpyrophosphate. The alkyl groups in the mentioned compounds preferably contain one to four carbon atoms.

Other suitable phosphorus-containing compounds include ammonium hydrogen phosphate, the phosphorus halides such as phosphorus trichloride, bromide, and iodide, alkyl phosphorodichloridites, $(RO)PCl_2$, dialkylphosphoro-chloridites, $(RO)_2PCl$, dialkylphosphinochloroidites, $R_2PCl$, alkyl alkylphosphonochloridates, $(RO)(R)P(O)Cl$, dialkyl phosphinochloridates, $R_2P(O)Cl$, and $RP(O)Cl_2$. Applicable corresponding sulfur derivatives include $(RS)PCl_2$, $(RS)_2PCl$, $(RS)(R)P(S)Cl$, and $R_2P(S)Cl$.

Particular phosphorus-containing compounds include ammonium phosphate, ammonium dihydrogen phosphate, diammonium hydrogen phosphate, diphenyl phosphine chloride, trimethylphosphite, phosphorus trichloride, phosphoric acid, phenyl phosphine oxychloride, trimethylphosphate, diphenyl phosphinous acid, diphenyl phosphinic acid, diethylchlorothiophosphate, methyl acid phosphate, and other alcohol-$P_2O_5$ reaction products.

Representative boron-containing compounds, which may be used to incorporate a boron oxide modifier into the catalysts disclosed herein, include boric acid, trimethylborate, boron oxide, boron sulfide, boron hydride, butylboron dimethoxide, butylboric acid, dimethylboric anhydride, hexamethylborazine, phenyl boric acid, triethylborane, diborane, and triphenyl boron.

Representative magnesium-containing compounds include magnesium acetate, magnesium nitrate, magnesium benzoate, magnesium propionate, magnesium 2-ethylhexoate, magnesium carbonate, magnesium formate, magnesium oxylate, magnesium bromide, magnesium hydride, magnesium lactate, magnesium laurate, magnesium oleate, magnesium palmitate, magnesium salicylate, magnesium stearate, and magnesium sulfide.

Representative calcium-containing compounds include calcium acetate, calcium acetylacetonate, calcium carbonate, calcium chloride, calcium methoxide, calcium naphthenate, calcium nitrate, calcium phosphate, calcium stearate, and calcium sulfate.

Representative lanthanum-containing compounds include lanthanum acetate, lanthanum acetylacetonate, lanthanum carbonate, lanthanum chloride, lanthanum hydroxide, lanthanum nitrate, lanthanum phosphate, and lanthanum sulfate.

The porous crystalline material employed in the embodiments disclosed herein may be combined with a variety of binder or matrix materials resistant to the temperatures and other conditions employed in the process. Such materials include active and inactive materials such as clays, silica and/or metal oxides such as alumina. The latter may be either naturally occurring or in the form of gelatinous precipitates or gels including mixtures of silica and metal oxides. Use of a material which is active, tends to change the conversion and/or selectivity of the catalyst and hence is generally not preferred. Inactive materials suitably serve as diluents to control the amount of conversion in a given process so that products can be obtained economically and orderly without employing other means for controlling the rate of reaction. These materials may be incorporated into naturally occurring clays, e.g., bentonite and kaolin, to improve the crush strength of the catalyst under commercial operating conditions. Said materials, i.e., clays, oxides, etc., function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst.

Naturally occurring clays which can be composited with the porous crystalline material include the montmorillonite and kaolin family, which families include the subbentonites, and the kaolins commonly known as Dixie, McNamee, Georgia, and Florida clays or others in which the main mineral constituent is halloysite, kaolinite, dickite, nacrite, or anauxite. Such clays can be used in the raw state as originally mined or initially subjected to calcination, acid treatment, or chemical modification.

In addition to the foregoing materials, the porous crystalline material can be composited with a porous matrix material such as silica-alumina, silica-magnesia, silica-zirconia, silica-thoria, silica-beryllia, silica-titania, as well as ternary compositions such as silica-alumina-thoria, silica-alumina-zirconia, silica-alumina-magnesia, and silica-magnesia-zirconia.

The relative proportions of porous crystalline material and inorganic oxide matrix vary widely, with the content of the former ranging from about 1 to about 90% by weight and more usually, particularly when the composite is prepared in the form of beads, in the range of about 2 to about 80 wt % of the composite.

The conditions employed in the alkylation stage of the present process are not narrowly constrained but, in the case of the methylation of toluene, generally include the following ranges: (a) temperature between about 500 and about 700° C., such as between about 500 and about 600° C.; (b) pressure of between about 1 atmosphere and about 1000 psig (between about 100 and about 7000 kPa), such as between about 10 psig and about 200 psig (between about 170 and about 1480 kPa); (c) moles toluene/moles methanol (in the reactor charge) of at least about 0.2, such as from about 0.2 to about 20; and (d) a weight hourly space velocity ("WHSV") for total hydrocarbon feed to the reactor(s) of about 0.2 to about 1000, such as about 0.5 to about 500 for the aromatic reactant, and about 0.01 to about 100 for the combined methanol reagent stage flows, based on total catalyst in the reactor(s).

The alkylation process can be conducted in any known reaction vessel but generally the methanol and aromatic feeds are contacted with the catalyst described above with the catalyst particles being disposed in one or more fluidized or fixed beds. Each of the methanol and aromatic feeds can be injected into the fluidized or fixed beds in a single stage. However, in one embodiment, the methanol feed is injected in stages into the fluidized or fixed beds at one or more locations downstream from the location of the injection of the aromatic reactant into the fluidized or fixed beds. For example, a fluidized bed reactor may be used, and the aromatic feed can be injected into a lower portion of a single vertical fluidized bed of catalyst, with the methanol being injected into the bed at a plurality of vertically spaced intermediate portions of the bed and the product being removed from the top of the bed. Alternatively, the catalyst can be disposed in a plurality of vertically spaced catalyst beds, with the aromatic feed being injected into a lower portion of the first fluidized bed and part of the methanol being injected into an intermediate portion of the first bed and part of the methanol being injected into or between adjacent downstream catalyst beds.

Typically, water is co-injected with the methanol feed to reduce the methanol partial pressure and minimize side reactions of methanol to olefin by-products. Methanol injected without a diluent, such as water, generally leads to a higher amount of light gas by-products. Diluting the methanol decreases the amount available for the side reactions upon introduction into the reactor.

An example of a preferred reaction vessel is disclosed in U.S. Pat. No. 9,095,831. Within the fluidized bed reactor, there is a primary and secondary cyclone for separating the fluidized catalyst particles from the gas flow, so that the gas (either reactor effluent or regenerator flue gas) can leave the vessel, and the catalyst can be returned back to the fluidized bed. The gas-solids mixture first passes through the primary cyclone, where the majority of the catalyst particles are separated and returned to the fluidized bed through the primary dipleg. The gas flow next passes through the secondary cyclone where additional catalyst particles are separated and returned to the fluidized bed through the secondary dipleg. When the recovered catalyst particles pass through the primary and secondary diplegs, typically steam is injected to fluidize the catalyst particles and further strip PX from the catalyst. However, as mentioned in the previous paragraph, steam can be harmful to the aging and activity rate of the catalyst. It should be appreciated that some embodiments may employ one or more cyclones that are disposed (at least partially) inside and/or outside of the reaction vessel.

The product of the reaction between the methanol and toluene and/or benzene is an alkylation effluent comprising PX and other xylene isomers, water vapor, unreacted toluene and/or benzene, unreacted methanol, phenolic impurities, and a variety of light gas by-products, such as $C_{4-}$ hydrocarbons, including paraffins, olefins, and contaminants such as nitrogen, nitrogen oxides, carbon monoxide, carbon dioxide, and oxygenates such as ethanal and dimethyl ether. The alkylation effluent will also generally contain some $C_{9+}$ aromatic by-products.

The alkylation effluent is fed through a series of separation steps where the alkylation effluent is first separated into a $C_{6+}$ hydrocarbon stream containing xylenes and a $C_{5-}$ hydrocarbon stream containing the light gas by-products. The $C_{6+}$ hydrocarbon stream may then be separated to recover the unreacted benzene and/or toluene and produce a $C_{8+}$ hydrocarbon stream, from which the heavy ($C_{9+}$) by-products may be separated to produce a $C_8$ hydrocarbon stream. PX is recovered from the $C_8$ hydrocarbon stream, typically by fractional crystallization or selective adsorption and the remaining $C_8$ hydrocarbons may be isomerized to produce more PX.

The $C_{5-}$ hydrocarbon stream containing the light gas by-products may be treated by a series of treatment steps, such as that disclosed in U.S. Patent Publication Nos. 2014/0100402 and 2016/0060187. In embodiments, the $C_{5-}$ hydrocarbon light gas stream goes through a series of wash steps, such as a methanol wash to remove oxygenates, a water wash to remove methanol, and a caustic wash to remove carbon dioxide. The light gas stream may then be dried to remove water, such as with a molecular sieve drier or by washing with methanol, which itself has preferably been dried to remove water, such as with a molecular sieve drier.

The dried light gas stream may then be sent to a fractionation tower primarily to remove dimethyl ether from the light olefins, so as to minimize the impact of dimethyl ether on olefins recovery equipment. Dimethyl ether can also be deleterious to a later-recovered propylene product by negatively impacting propylene in downstream processes such as polymerization. The fractionation tower acts to fractionate the light gas stream into an overhead stream, containing at least some, and preferably most, of the $C_{3-}$ hydrocarbons, and almost all of the dimethyl ether and $C_{4+}$ hydrocarbons as a liquid bottoms stream. For example, ethylene and at least about 80 wt %, preferably at least about 90 wt %, of the propylene, and about 67 wt % of the propane from the fractionation column are recovered in the overhead stream, while nearly 100 wt % of the dimethyl ether and nearly 100 wt % of $C_{4+}$ hydrocarbons are removed in the liquid bottoms stream. The overhead vapor stream from the fractionation tower, which generally comprises less than about 100 ppm dimethyl ether, preferably 20 ppm or less by weight, more preferably 1 ppm or less by weight is sent to a contaminant removal system, and the recovered dimethyl ether may be recycled to the methylation reaction.

The overhead stream from the fractionation tower may be treated to remove the contaminants from the light gas stream as described in U.S. Patent Publication No. 2016/0060187. The contaminant-free light gas stream may be sent to olefins recovery to recover at least the valuable olefinic component of the stream, but in one embodiment, the light gas stream, including olefins, is recycled to the methylation reaction to decrease the amount of water and/or steam necessary. When the light gas stream is recycled to be used as a diluent for the methanol introduction, the light gas stream may be recycled to the reactor with any combination of the above treatment steps, or without being subjected to any of the above-mentioned treatment steps. That is, the $C_{5-}$ hydrocarbon stream containing the light gas by-products separated from the alkylation effluent may be recycled to the reactor without removing oxygenates, methanol, carbon dioxide, water, or dimethyl ether, or after removing any one of the contaminants, or after removing any combination of the contaminants.

In one embodiment, light gas, preferably recycled light gas from the alkylation effluent, including olefins, is co-injected with the methanol alkylating agent into the alkylation reaction to reduce the methanol partial pressure at the injection points. Another benefit of co-injecting an olefin-rich light gas with the methanol is the higher utilization of the methanol in the aromatic alkylation reaction rather than the methanol reacting to form olefin by-products. In an embodiment, the molar ratio of light gas to methanol is maintained in the range of 0.01:1 to 20:1. The methanol/light gas mixture may be injected into a single stage or into multiple stages axially along the reactor. The total rate of methanol/light gas mixture and the methanol/light gas mixture molar ratio injected into each stage may be held constant or varied in each stage to optimize reactor yields. In other embodiments, water and light gas may be co-injected with the methanol.

In another embodiment, light gas, preferably recycled light gas from the alkylation effluent, is used, partially or totally, in place of steam to fluidize the catalyst particles being reintroduced into the catalyst bed from the primary and secondary diplegs of the primary and secondary internal reactor cyclones.

Using light gas in place of water or steam in these instances reduces the amount of water and steam present in the reactor, extending the life of the catalyst and further promoting the reaction of methanol in the aromatics alkylation reaction rather than in the formation of olefins. Water vaporizes in the reactor, forming steam, which negatively affects the activity of the catalyst. Water/steam also competes for available acid sites on the catalyst, affecting catalyst performance and PX selectivity. Additionally, water is a product of the desired reaction, so introducing water may negatively influence the desired reaction. Using recycled light gas from the alkylation effluent as the light gas source allows the downstream separation equipment to be reduced.

While the present invention has been described and illustrated by reference to particular embodiments, those of ordinary skill in the art will appreciate that the invention lends itself to variations and modifications not necessarily illustrated herein without departing from the spirit and scope of the invention. Accordingly, it is not intended that the scope of the claims appended hereto be limited to the examples and descriptions set forth herein but rather that the claims be construed as encompassing all the features of patentable novelty which reside herein, including all features which would be treated as equivalents thereof by those skilled in the art to which this disclosure pertains.

Trade names used herein are indicated by a ™ symbol or ® symbol, indicating that the names may be protected by certain trademark rights, e.g., they may be registered trademarks in various jurisdictions. All patents and patent applications, test procedures (such as ASTM methods, UL methods, and the like), and other documents cited herein are fully incorporated by reference to the extent such disclosure is not inconsistent with this invention and for all jurisdictions in which such incorporation is permitted. When numerical lower limits and numerical upper limits are listed herein, ranges from any lower limit to any upper limit are contemplated. The term "comprising" is synonymous with the term "including". Likewise whenever a composition, an element or a group of components is preceded with the transitional phrase "comprising," it is understood that we also contemplate the same composition or group of components with transitional phrases "consisting essentially of," "consisting of," "selected from the group of consisting of," or "is" preceding the recitation of the composition, component, or components, and vice versa.

What we claim:

1. A process for alkylation of toluene and/or benzene to produce paraxylene (PX) comprising contact of said toluene and/or benzene with an alkylating agent selected from methanol, dimethyl ether, and mixtures thereof, in the absence of intentionally co-fed molecular hydrogen, in the presence of an alkylation catalyst in a fluidized bed alkylation reactor under conditions effective to produce an alkylation effluent comprising PX and olefins, wherein the alkylation effluent is separated into a stream comprising PX and a light gas stream comprising olefins, the process comprising recycling at least a portion of the light gas stream, including olefins and substantially free of molecular hydrogen, to the alkylation reactor for injection with the alkylating agent, fluidizing particles of the alkylation catalyst that are recovered from the alkylation effluent in the alkylation reactor, or both.

2. The process of claim 1, wherein the light gas stream further comprises oxygenates, unreacted alkylating agent, and contaminants, and is treated to remove at least one of the oxygenates, alkylating agent, and contaminants prior to recycling the light gas stream to the alkylation reactor.

3. The process of claim 1, wherein the alkylating agent is methanol.

4. The process of claim 3, wherein the methanol and recycled light gas stream is injected in multiple stages axially along the alkylation reactor.

5. The process of claim 2, wherein a molar ratio of light gas stream to methanol is maintained in a range of 0.01:1 to 20:1.

6. The process of claim 1, wherein the alkylation reactor comprises at least one internal cyclone with a dipleg for separating particles of the alkylation catalyst from the alkylation effluent, and the light gas stream is used to fluidize the catalyst particles being discharged from the dipleg.

7. The process of claim 1, wherein the alkylation catalyst is a porous crystalline material having a Diffusion Parameter for 2,2 dimethylbutane of about 0.1-15 sec$^{-1}$ when measured at a temperature of 120° C. and a 2,2 dimethylbutane pressure of 60 torr (8 kPa).

8. The process of claim 7, wherein the alkylation catalyst is a medium-pore size aluminosilicate zeolite selected from the group consisting of ZSM-5, ZSM-11, ZSM-12, ZSM-22, ZSM-23, ZSM-35, and ZSM-48, optionally composited with an inorganic oxide matrix.

9. A process for producing paraxylene (PX), the process comprising:
(a) contacting toluene and/or benzene with methanol in the presence of an alkylation catalyst in an alkylation reactor in the absence of intentionally co-fed molecular hydrogen under conditions effective to produce an alkylation effluent comprising PX and olefins;
(b) separating the alkylation effluent into a product stream containing PX and a light gas stream containing olefins;
(c) recovering PX from the product stream; and
(d) recycling at least a portion of the light gas stream, including olefins and substantially free of molecular hydrogen, to the alkylation reactor for at least one of the following:
(i) injection with the methanol, or
(ii) fluidizing particles of the alkylation catalyst that are recovered from the alkylation effluent in the alkylation reactor.

10. The process of claim 9, wherein the light gas stream further comprises oxygenates, unreacted alkylating agent, and contaminants, and is treated to remove at least one of the oxygenates, alkylating agent, and contaminants prior to recycling the light gas stream to the alkylation reactor.

11. The process of claim 9, wherein the methanol and recycled light gas stream is injected in multiple stages axially along the alkylation reactor.

12. The process of claim 9, wherein a molar ratio of light gas to methanol is maintained in a range of 0.01:1 to 20:1.

13. The process of claim 9, wherein the alkylation reactor comprises at least one cyclone with a dipleg for separating particles of the alkylation catalyst from the alkylation effluent, and the light gas stream is used to fluidize the catalyst particles being discharged from the dipleg.

14. The process of claim 9, wherein the alkylation catalyst is a porous crystalline material having a Diffusion Parameter for 2,2 dimethylbutane of about $0.1\text{-}15\ \text{sec}^{-1}$ when measured at a temperature of 120° C. and a 2,2 dimethylbutane pressure of 60 torr (8 kPa).

15. The process of claim 14, wherein the alkylation catalyst is a medium-pore size aluminosilicate zeolite selected from the group consisting of ZSM-5, ZSM-11, ZSM-12, ZSM-22, ZSM-23, ZSM-35, and ZSM-48, optionally composited with an inorganic oxide matrix.

\* \* \* \* \*